United States Patent [19]

Masaki et al.

[11] Patent Number: 5,053,402
[45] Date of Patent: Oct. 1, 1991

[54] CERTAIN GLYCERYL PHOSPHATE-CYCLIC AMMONIUM COMPOUNDS USEFUL FOR TREATING HYPERTENSION

[75] Inventors: Mitsuo Masaki, Chiba; Hiromitsu Takeda, Washimiya; Toshiro Kamishiro; Masao Yamamoto, both of Misato, all of Japan

[73] Assignee: Nippon Chemiphar Co., Ltd., Tokyo, Japan

[21] Appl. No.: 438,996

[22] Filed: Nov. 22, 1989

Related U.S. Application Data

[63] Continuation of Ser. No. 73,556, Jul. 14, 1987, abandoned.

[30] Foreign Application Priority Data

Jul. 14, 1986 [JP] Japan .................. 61-165330
Mar. 17, 1987 [JP] Japan .................. 62-62194

[51] Int. Cl.$^5$ .................. C07F 9/59; C07F 9/38; C07F 9/553; A61K 31/675
[52] U.S. Cl. .................. 514/79; 514/89; 514/91; 540/450; 540/542; 546/25; 548/413
[58] Field of Search ............ 546/25; 548/413; 540/542, 450; 514/79, 89, 91

[56] References Cited

U.S. PATENT DOCUMENTS 4,710,579 12/1987 Nojima et al. .................. 558/169

FOREIGN PATENT DOCUMENTS 0070433 1/1983 European Pat. Off. .............. 546/22

OTHER PUBLICATIONS

LIPIDS, vol. 3, No. 3, 1968, pp. 228-233; D. L. Turner et al.: "The Total Synthesis of Phosphatidyl(Dioleoyl)-Hydroxy-L-Proline and its Activity in Blood-Clotting Systems".
European Journal of Pharmacology, vol. 131, 1986, pp. 179-188, Elsevier Science Publishers B.V.; E. Coeffier et al.: "Effects of PAF-Acether Structural Analogues on Platelet Activation and Bronchoconstriction in Guinea-Pigs".
"Chemical Abstracts" 84:58255n.
"Chemical Abstracts" 51,210c.

Primary Examiner—Alan L. Rotman
Attorney, Agent, or Firm—Sixbey, Friedman, Leedom & Ferguson

[57] ABSTRACT

A glycerol derivative which is effective to reduce blood pressure and has the formula:

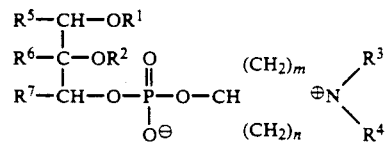

wherein $R^1$ is an alkyl group having 10-22 carbon atoms, $R^2$ is a lower acyl group or benzoyl, each of $R^3$ and $R^4$ independently is hydrogen or a straight or branched chain alkyl group having 1-6 carbon atoms; each of $R^5$, $R^6$ and $R^7$ independently is hydrogen, a straight or branched chain alkyl group having 1-6 carbon atoms, an aryl group or an aralkyl group; and each of m and n independently is 0 or a positive integer under the condition of m+n=2-8.

19 Claims, No Drawings

CERTAIN GLYCERYL PHOSPHATE-CYCLIC AMMONIUM COMPOUNDS USEFUL FOR TREATING HYPERTENSION

This application is a continuation of Ser. No. 07/073,556, filed July 14, 1987, now abandoned.

BACKGROUND OF THE INVENTION

1. Field of the Invention

The present invention relates to a novel glycerol derivative, a process for the preparation of the same and an anti-hypertensive agent containing the glycerol derivative.

2. Description of Prior Art

Recently, studies of platelet activating factor (PAF) have been advanced, and its physiological function has been made clear. According to the studies, in living body, PAF shows functions relating to allergy, inflammation, and platelet agglutination, and also PAF shows strong blood pressure reducing action (Nature, vol. 285, 193(1980), and European Journal of Pharmacology, 65, 185-192(1980)).

Therefore, studies have been further made for utilizing the excellent blood pressure reducing action of PAF with removal or reduction of its unfavorable effects such as platelet agglutinating action.

As compounds functioning as PAF, there are known certain glycerol derivatives. Accordingly, extensive studies have been made for discovering new glycerol derivatives having the improved action.

SUMMARY OF THE INVENTION

Accordingly, the present invention has an object to provide a new glycerol derivative which shows a prominent blood pressure reducing action with reduced unfavorable actions such as reduced platelet aggregating action and to provide a process for the preparation of the glycerol derivative.

The invention has another object to provide a new glycerol derivative which shows an anti-tumor action.

The invention has a further object to provide an anti-hypertensive agent utilizing the above-mentioned new glycerol derivative.

There is provided by the present invention a glycerol derivative having the formula (I):

$$\begin{array}{c} R^5-CH-OR^1 \\ | \\ R^6-C-OR^2 \quad O \quad (CH_2)_m \quad R^3 \\ | \quad \quad \| \quad \quad \diagup \\ R^7-CH-O-P-O-CH \quad \oplus N \\ | \quad \quad \quad \quad \diagdown \\ O^\ominus \quad (CH_2)_n \quad R^4 \end{array} \quad (I)$$

wherein
$R^1$ is a straight or branched chain alkyl group having 10–22 carbon atoms;
$R^2$ is a straight or branched chain acyl group having 1–6 carbon atoms or benzoyl;
each of $R^3$ and $R^4$ independetly is hydrogen or a straight or branched chain alkyl group having 1–6 carbon atoms;
each of $R^5$, $R^6$ and $R^7$ independently is hydrogen, a straight or branched chain alkyl group having 1–6 carbon atoms, an aryl group or an aralkyl group; and
each of m and n independently is zero(0) or a positive integer under the condition of $m+n=2-8$.

The glycerol compound having the formula (I) can be prepared by a process which comprises acylating a compound having the formula (II):

$$\begin{array}{c} R^5-CH-OR^1 \\ | \\ R^6-C-OH \quad O \quad (CH_2)_m \quad R^3 \\ | \quad \quad \| \quad \quad \diagup \\ R^7-CH-O-P-O-CH \quad \oplus N \\ | \quad \quad \quad \quad \diagdown \\ O^\ominus \quad (CH_2)_n \quad R^4 \end{array} \quad (II)$$

wherein each of $R^1$, $R^3$, $R^4$, $R^5$, $R^6$, $R^7$, m and n independently has the same meaning as above,
with an acylating agent containing the group $R^2$ that is a straight or branched chain acyl group having 1–6 carbon atoms or benzoyl.

The glycerol compound having the formula (I) can be also prepared by a process which comprises reacting a compound having the formula (X):

$$\begin{array}{c} R^5-CH-OR^1 \\ | \\ R^6-C-OR^2 \\ | \\ R^7-CH-OH \end{array} \quad (X)$$

wherein each of $R^1$, $R^2$, $R^5$, $R^6$ and $R^7$ independently has the same meaning as above,
with phosphorus oxychloride (i.e., phosphoryl chloride) and a compound having the formula (V):

$$\begin{array}{c} (CH_2)_m \quad R^3 \\ \diagup \\ H-O-CH \quad \oplus N \quad A^\ominus \\ \diagdown \\ (CH_2)_n \quad R^4 \end{array} \quad (V)$$

wherein each of $R^3$, $R^4$, m and n has the same meaning as above, and $A^\ominus$ is an anion
in the presence of a base.

DETAILED DESCRIPTION OF THE INVENTION

In the formula (I), $R^1$ represents a straight or branched chain alkyl group having 10–22 carbon atoms such as decyl, undecyl, tridecyl, tetradecyl, pentadecyl, hexadecyl, heptadecyl, octadecyl, nonadecyl, eicosyl, heneicosyl or docosyl. $R^1$ preferably is a straight or branched chain alkyl having 12–20 carbon atoms.

$R^2$ represents a straight or branched chain acyl having 1–6 carbon atoms such as formul, acetyl, propionyl, butyryl, isobutyryl, valeryl, isovaleryl or pivaloyl, or benzoyl. $R^2$ preferably is a straight chain acyl group having 2–6 carbon atoms.

$R^3$ and $R^4$ are the same as or different from each other, and each independently represents hydrogen or a straight or branched chain alkyl group having 1–6 carbon atoms such as methyl, ethyl, n-propyl, isopropyl, n-butyl, isobutyl, pentyl or hexyl.

$R^5$, $R^6$ and $R^7$ are the same as or different from each other, and each independently represents hydrogen or a straight or branched chain alkyl group having 1–6 carbon atoms such as methyl, ethyl, n-propyl, isopropyl, n-butyl, isobutyl, pentyl or hexyl, an aryl group such as phenyl or a substituted phenyl (e.g., toluyl or xylyl), or an aralkyl group preferably having an alkylene bonding of 1–3 carbon atoms such as benzyl or phenylethyl. In preferred embodiments, (1) $R^5$, $R^6$ and $R^7$ are all hydrogens, (2) $R^5$ is a straight or branched chain alkyl group having 1-6 carbon atoms and $R^6$ and $R^7$ are both hydrogens, and (3) $R^7$ is a straight or branched chain alkyl group having 1-6 carbon atoms and $R^5$ and $R^6$ are both hydrogens.

Each of m and n independently is 0 or a positive integer under the condition of m+n=2-8 (preferably m+n=3-5).

An example of of the heterocyclic group of the formula (I) is a quaternary salt of pyrrolidinyl, piperidinyl or perhydroazepinyl which has the substitutent groups of $R^3$ and $R^4$.

Examples of the glycerol derivatives having the formula (I) are as follows:

(1) 2-acetyloxy-3-hexadecyloxypropyl 1,1-dimethylpiperidinio-3-yl phosphate;
(2) 2-acetyloxy-3-hexadecyloxypropyl 1,1-diethylpiperidinio-3-yl phosphate;
(3) 3-hexadecyloxy-2-propiyonyloxypropyl 1,1-dimethylpiperidinio-3-yl phosphate;
(4) 2-benzoyloxy-3-hexadecyloxypropyl 1,1-dimethylpiperidinio-3-yl phosphate;
(5) 2-acetyloxy-3-octadecyloxypropyl 1,1-dimethylpiperidinio-3-yl phosphate;
(6) 2-acetyloxy-3-octadecyloxypropyl 1,1-diethylpiperidinio-3-yl phosphate;
(7) 2-acetyloxy-3-heptadecyloxypropyl 1,1-dimethylpiperidinio-3-yl phosphate;
(8) 2-acetyloxy-3-nonadecyloxypropyl 1,1-dimethylpiperidinio-3-yl phosphate;
(9) 2-acetyloxy-3-hexadecyloxypropyl 1-methyl-3-piperidinyl phosphate;
(10) 2-acetyloxy-3-hexadecyloxypropyl 1-ethyl-1-methylpiperidinio-3-yl phosphate;
(11) 2-acetyloxy-3-hexadecyloxybutyl 1,1-dimethylpiperidinio-3-yl phosphate;
(12) 2-acetyloxy-3-octadecyloxybutyl 1,1-dimethylpiperidinio-3-yl phosphate;
(13) 2-acetyloxy-3-hexadecyloxy-1-methylbutyl 1,1-dimethylpiperidinio-3-yl phosphate;
(14) 2-acetyloxy-3-hexadecyloxy-1-methylpropyl 1,1-dimethylpiperidinio-3-yl phosphate;
(15) 2-acetyloxy-3-hexadecyloxy-1-(1-methylethyl)butyl 1,1-dimethylpiperidinio-3-yl phosphate;
(16) 2-acetyloxy-3-hexadecyloxy-2-methylpropyl 1,1-dimethylpiperidinio-3-yl phosphate;
(17) 2-acetyloxy-3-hexadecyloxypropyl 1-methyl-1-propylpiperidinio-3-yl phosphate;
(18) 2-acetyloxy-3-hexadecyloxypropyl 1,1-dimethylpiperidinio-4-yl phosphate;
(19) 2-acetyloxy-3-hexadecyloxypropyl 1,1-diethylpiperidinio-4-yl phosphate;
(20) 3-hexadecyloxy-2-propionyloxypropyl 1,1-dimethylpiperidinio-4-yl phosphate;
(21) 2-benzoyloxy-3-hexadecyloxypropyl 1,1-dimethylpiperidinio-4-yl phosphate;
(22) 2-acetyloxy-3-octadecyloxypropyl 1,1-dimethylpiperidinio-4-yl phosphate;
(23) 2-acetyloxy-3-hexadecyloxybutyl 1,1-dimethylpiperidinio-4-yl phosphate;
(24) 2-acetyloxy-3-octadecyloxybutyl 1,1-dimethylpiperidinio-4-yl phosphate;
(25) 2-acetyloxy-3-hexadecyloxy-1-methylbutyl 1,1-dimethylpiperidinio-4-yl phosphate;
(26) 2-acetyloxy-3-hexadecyloxy-2-methylpropyl 1,1-dimethylpiperidinio-4-yl phosphate;
(27) 2-acetyloxy-3-hexadecyloxy-1-(1-methylethyl)propyl 1,1-dimethylpiperidinio-4-yl phosphate;
(28) 2-acetyloxy-3-hexadecyloxypropyl 1,1-dimethylpyrrolidinio-3-yl phosphate;
(29) 2-acetyloxy-3-hexadecyloxypropyl 1,1-diethylpyrrolidinio-3-yl phosphate;
(30) 3-hexadecyloxy-2-propionyloxypropyl 1,1-dimethylpyrrolidinio-3-yl phosphate;
(31) 2-benzoyloxy-3-hexadecyloxypropyl 1,1-dimethylpyrrolidinio-3-yl phosphate;
(32) 2-acetyloxy-3-octadecyloxypropyl 1,1-dimethylpyrrolidinio-3-yl phosphate;
(33) 2-acetyloxy-3-hexadecyloxybutyl 1,1-dimethylpyrrolidinio-3-yl phosphate;
(34) 2-acetyloxy-3-octadecyloxybutyl 1,1-dimethylpyrrolidinio-3-yl phosphate;
(35) 2-acetyloxy-3-hexadecyloxy-1-methylbutyl 1,1-dimethylpyrrolidinio-3-yl phosphate;
(36) 2-acetyloxy-3-hexadecyloxy-1-methylpropyl 1,1-dimethylpyrrolidinio-3-yl phosphate;
(37) 2-acetyloxy-3-hexadecyloxy-2-methylpropyl 1,1-dimethylpyrrolidinio-3-yl phosphate;
(38) 2-acetyloxy-3-hexadecyloxypropyl 1,1-dimethylperhydroazepinio-3-yl phosphate; and
(39) 2-acetyloxy-3-hexadecyloxybutyl 1,1-dimethylperhydroazepinio-3-yl phosphate.

The compounds having the formula (I) of the present invention may be in the form of a variety of isomers arising from the presence of asymmetric carbons.

The compound of the formula (I) can be prepared by prepared by acylating a compound having the formula (II):

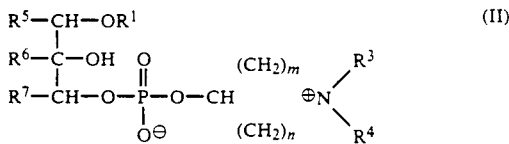

wherein each of $R^1$, $R^3$, $R^4$, $R^5$, $R^6$, $R^7$, m and n independently has the same meaning as above, with an acylating agent containing the group $R^2$ that is a straight or branched chain acyl group having 1-6 carbon atoms or benzoyl.

Generally, the acylating agent is an acid anhydride ($R^2$—O—$R^2$) or an acyl chloride ($R^2$—Cl).

The acylating reaction can be carried out in an appropriate organic solvent in the presence of a base. The base may be an ordinary base such as pyridine or triethylamine. If necessary, a catalyst such as 4-dimethylaminopyridine may be employed. Examples of the organic solvents include halogenated hydrocarbons such as methylene chloride, ethylene chloride, chloroform, carbon tetrachloride. In place of using an organic solvent, the acylating agent or a base can be employed as a solvent.

There are no specific limitations with respect to the reaction temperature and the reaction period. Generally, the reaction temperature ranges from 0° C. to a boiling point of a solvent employed, and the reaction period ranges from 30 minutes to 24 hours.

After the acylating reaction is complete, the solvent is distilled off, and if necessary then purified by chromatography using silica gel, to obtain a desired compound as a pure product.

The above-mentioned stargting compound of the formula (II) is a novel compound and can be prepared by the following steps:

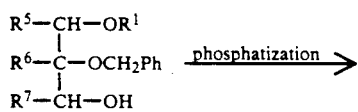

(III)

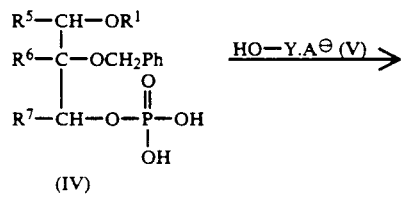

(IV)

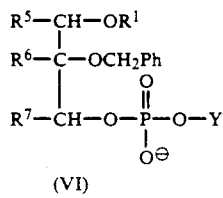

(VI)

In the above formulae, Ph is phenyl, $A^\ominus$ is an anion such as chlorine ion, bromine ion, iodine ion or tosyl ion, each of $R^1$, $R^5$, $R^6$ and $R^7$ independently has the same meaning as above, and Y is a group having the following formula.

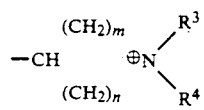

A starting compound having the formula (III) wherein $R^1$ is hexadecyl, and each of $R^5$, $R^6$ and $R^7$ is hydrogen is already known as described in D. Arnold et al., Liebigs Ann. Chem., Vol. 709, pp. 234–239(1967). Other compounds represented by the formula (III) can be prepared in similar manners to those described in the above publication.

The phosphatization can be carried out using a phosphatizing agent such as phosphorus oxychloride, and the phosphatized product is then reacted with a compound of the formula (V). The phosphatized product can be hydrolyzed and reacted with a compound of the formula (V) in the presence of an activator for phosphoric acid such as trichloroacetonitrile. After the reaction is complete, the resulting product is treated with an ion exchange resin or a silver salt such as silver carbonate or silver acetate to yield a compound of the formula (VI).

The compound of the formula (VI) is then subjected to catalytic reduction for removing its benzyl group to yield a compound of the formula (II). The catalytic reduction can be carried out under hydrogen atmosphere in the presence of a hydrogenation catalyst such as palladium-carbon, palladium black or platinum dioxide.

The reactions described above are essentially known, and a solvent, a reaction temperature and a reaction period can be chosen according to the known conditions.

Alternatively, the compound of the formula (I) according to the present invention can be prepared by other processes. For instance, the compound of the formula (I) can be prepared by reacting a compound having the formula (X):

wherein each of $R^1$, $R^2$, $R^5$, $R^6$ and $R^7$ independently has the same meaning as above, with phosphorus oxychloride (i.e., phosphoryl chloride) and a compound having the formula (V):

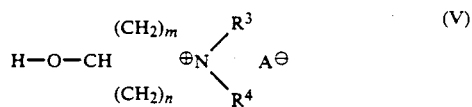

wherein each of $R^3$, $R^4$, m and n has the same meaning as above, and $A^\ominus$ is an anion in the presence of a base.

The above alternative process can be carried out by the following steps:

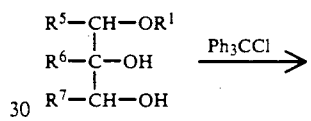

(VII)

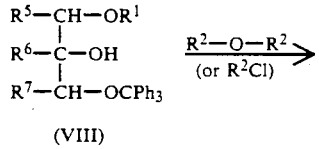

(VIII)

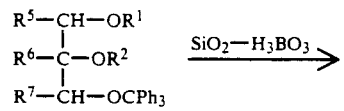

(IX)

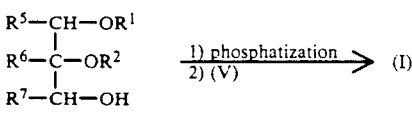

(X)

In the above formulae, each of $R^1$, $R^2$, $R^5$, $R^6$ and $R^7$ independently has the same meaning as above, and Ph is phenyl. The above process comprises a step of acylation in advance of a step of phosphatization.

A compound in the "sn" form having the formula (X) wherein $R^1$ is hexadecyl, and each of $R^5$, $R^6$ and $R^7$ is hydrogen is already known as described in Synthesis, 1982, pp. 399–402. Other compounds represented by the formula (X) can be prepared in similar manners to those described in the above publication.

The reactions described above are essentially known, and a solvent, a reaction temperature and a reaction period can be chosen according to the known conditions.

Blood pressure reducing actions and blood platelet agglutination action of the glycerol derivatives of the present invention are described by the following pharmacological experimental data.

Blood Pressure Reducing Action: Intravenous Injection

[Procedure]

Male Wister rats (mean body weight: 420 g) were anesthetized by intra-peritoneal injection of 50 mg/kg of pentobarbital sodium and were fixed on their backs, and their blood pressures were measured at left femoral artery. Subsequently, a compound to be tested was dissolved in a saline solution containing 0.25% bovine serum albumin and injected into the rat through the right femoral vein.

[Experimental Results]

Compound: 2-Acetyloxy-3-hexadecyloxypropyl 1,1-dimethylpyrrolidinio-3-yl phosphate (Example 8 given hereinafter)

| Administered Amount (ng/kg) | Number of Samples | Blood Pressure before Administration (mmHg) | Reduction of Blood Pressure (mmHg) |
| --- | --- | --- | --- |
| 100 | 3 | 121 | $-67.0 \pm 3.1$ |
| 50  | 4 | 122 | $-52.6 \pm 4.6$ |
| 10  | 2 | 112 | $-47.5 \pm 0.5$ |
| 5   | 2 | 119 | $-21.5 \pm 8.0$ |
| 1   | 2 | 136 | $-4.5 \pm 1.5$ |

A dose-response curve was prepared from the above values to determine a dose required for reducing average blood pressure by 50 mmHg ($MABP_{50}$). $MABP_{50}$ for the above compound was 21 ng/kg.

$MABP_{50}$ values determined for other compounds of the present invention are given below:

(A) 2-acetyloxy-3-hexadecyloxypropyl 1,1-dimethylpiperidinio-3-yl phosphate (Example 1 given hereinafter): $MABP_{50} = 13$ ng/kg (B) 2-acetyloxy-3-hexadecyloxypropyl 1,1-dimethylpiperidinio-4-yl phosphate (Example 2): $MABP_{50} = 58$ ng/kg (C) 3-acetyloxy-2-hexadecyloxybutyl 1,1-dimethylpyrrolidinio-3-yl phosphate (Example 3): $MABP_{50} = 8.5$ ug/kg (D) 2-acetyloxy-3-hexadecyloxybutyl 1,1-dimethylpiperidinio-3-yl phosphate (Example 4): $MABP_{50} = 340$ ng/kg (E) 2-acetyloxy-3-hexadecyloxybutyl 1,1,-dimethylpiperidinio-4-yl phosphate (Example 5): $MABP_{50} = 8.6$ ug/kg (F) 2-acetyloxy-3-hexadecyloxy-1-(1-methylethyl)propyl 1,1-dimethylpyrrolidinio-3-yl phosphate (Example 6): $MABP_{50} = 48$ μg/kg Blood Pressure Decreasing Action: Oral Administration

[Procedure]

Spontaneously hypertensive male rates (average body weight: 359 g) were etherized and fixed on their backs. Blood pressure was measured for each rat through cannulation at its left femoral artery. A compound to be tested was dissolved in a distilled water and the resulting aqueous solution was administered orally.

| Compound | None | C | D | E |
| --- | --- | --- | --- | --- |
| Dose (mg/kg) | — | 10 | 10 | 10 |
| Number of Sample | 2 | 3 | 3 | 2 |
| Blood Pressure | 155.0 | 175.7 | 160.0 | 140.5 |

| Compound | None | C | D | E |
| --- | --- | --- | --- | --- |
| before Administration (mmHg) | | | | |
| Reduction of Blood Pressure (mmHg) | | | | |
| After 30 min. | +5.0 | −49.7 | −66.0 | +5.0 |
| After 1 hr. | +6.0 | −60.7 | −68.0 | 0 |
| After 2 hrs. | +3.5 | −74.3 | −73.0 | −14.5 |
| After 3 hrs. | +2.0 | −82.0 | −72.3 | −19.0 |
| After 4 hrs. | — | −84.7 | −66.7 | −22.5 |
| After 5 hrs. | — | −83.7 | −63.0 | −26.0 |
| After 6 hrs. | — | −82.3 | −66.7 | −28.0 |

Remark:
Compounds C, D and E are the same as described above.

Blood Platelet Agglutination Action

[Procedure]

A male Japanese white rabbit was anesthetized by pentobarbital, and a blood was collected in aqueous 3.13% sodium citrate solution at its carotid. The blood containing 1/10 volume ratio of the sodium citrate solution was treated in a conventional manner to give a platelet rich plasma (PRP) and a platelet poor plasma (PPP) for performing the following experiment.

PRP was diluted with PPP to give a sample containing platelets at $300,000/mm^3$.

Agglutination of platelet was determined by means of Platelet Aggregation Tracer PAT-4A (available from Niko Bioscience Co., Ltd., Japan). 10 μl of a test solution was added to 190 μl of PRP to give a final solution of $2 \times 10^{-10}$ to $2 \times 10^{-4}$ M, and an agglutination curve is recorded. For the preparation of the test solution, a saline solution containing 0.25% bovine serum albumin.

[Results]

Compound: 2-Acetyloxy-3-hexadecyloxypropyl 1,1-dimethylpyrrolidinio-3-yl phosphate (Example 8)

| Concentration (M) | Agglutination of Platelet (%) |
| --- | --- |
| $2 \times 10^{-6}$ | 86 |
| $2 \times 10^{-7}$ | 81 |
| $2 \times 10^{-8}$ | 67 |
| $2 \times 10^{-9}$ | 18 |
| $2 \times 10^{-10}$ | 0 |

Remark:
Agglutination of Platelet
PRP = 0%, PPP = 100%

The agglutination curve indicated that $EC_{50}$ value was $1.8 \times 10^{-8}$ M.

The above-mentioned compounds A to F were also evaluated on agglutination action by preparing agglutination curves. The results are set forth in the following Table.

| Compound | $EC_{50}$ |
| --- | --- |
| A | $6.0 \times 10^{-10}$ |
| B | $8.0 \times 10^{-9}$ |
| C | $4.0 \times 10^{-7}$ |
| D | $2.2 \times 10^{-8}$ |
| E | $6.3 \times 10^{-7}$ |
| F | $5.0 \times 10^{-6}$ |

As is clear from the above experimental data, the glycerol derivatives of the present invention show prominent blood pressure reducing action, while show troublesome blood platelet agglutination action at a lower level.

The glycerol derivative of the present invention can be used as a pharmaceutical composition in the form of tablets, granules, powder, capsule, syrup, suppository, injection liquid etc. The glycerol derivative is generally adiminstered to human being at a dose of 10 μg/kg to 0.5 mg/kg. The pharmaceutical composition of such dose can be administered 1-4 times a day depending on conditions of patients. Thus, the dose can vary depending upon conditions of patient, procedure of administration, etc. The pharmaceutical compositions can contain a carrier, a vehicle, a diluent, etc.

The processes for the preparation of the glycerol derivatives of the present invention and the pharmaceutical compositions are further described by the following examples. The phosphates expressed in the following examples are in the form of inner salts. The reference examples are given to describe starting compounds and intermediate compound employed for the preparation of the glycerol derivatives of the present invention.

REFERENCE EXAMPLE 1

1,1-Dimethyl-3-hydroxypiperidinium p-toluenesulfonate

In 20 ml of acetone was dissolved 2.30 g of 1-methyl-3-piperidinol, and 3.72 g of methyl p-toluenesulfonate was added dropwise to the resulting solution. The mixture was stirred at room temperature, heated under reflux, and cooled to precipitate crystals. The crystals were collected by filtration and dried to give 4.94 g of the desired product, m.p. 125°-127° C. (decomp.).

$^1$H NMR (DMSO-d$_6$) δ: 1.05-2.0 (m, 4H), 2.28 (s, 3H), 3.04 (s, 3H), 3.15 (s, 3H), 2.6-3.6 (m, 4H), 3.7-4.1 (m, 1H), 5.40 (d, 1H), 6.9-7.55 (m, 4H)

IR (KBr) cm$^{-1}$: 3400, 3040, 3000, 2950, 1450, 1180, 1120, 1035, 1010, 810, 680

REFERENCE EXAMPLE 2

2-Benzyloxy-3-hexadecyloxypropyl 1,1-dimethylpiperidinio-3-yl phosphate

In 3 ml of chloroform having been passed through alumina were dissolved 0.12 ml of phosphorus oxychloride and 0.35 ml of triethylamine under nitrogen atmosphere, and the resulting solution was stirred for a while at room temperature. To the solution was dropwise added under chilling 3 ml of solution of 407 mg of 2-benzyloxy-3-hexadecyloxy-1-propanol in chloroform (treated as above). After the addition was complete, the mixture was stirred for 30 minutes at room temperature, and to the mixture were added 452 mg of the quaternary salt prepared in Reference Example 1 and 10 ml of dry pyridine. The mixture was stirred overnight at room temperature, and to the mixture were added 560 mg of sodium hydrogencarbonate and 1.25 ml of water. The solvent was then distilled off under reduced pressure. To the residue was added 15 ml of a mixture of toluene and methylene chloride (v/v=1/1), and the insolubles were filtered off. The mother liquer was concentrated under reduced pressure, and the resulting residue was dissolved in a mixture of tetrahydrofuran and water (v/v=95/5). The solution was passed through a column of ion-exchange resin (Amberlite MB-3), which was then eluated with the same mixture of tetrahydrofuran and water. The eluate was placed under reduced pressure to distill off the solvent. The residue was purified by column chromatography using silica gel (eluent: chloroform/methanol/water=70/30/5) to obtain 293 mg of the desired compound.

$^1$H NMR (CD$_3$OD) δ: 0.89 (t, 3H), 1.28 (s, 26H), 1.3-4.6 (m, 24H), 4.69 (s, 2H), 7.15-7.45 (m, 5H)

IR (KBr) cm$^{-1}$: 3400, 3060, 3025, 2920, 2850, 1460, 1220, 1080, 1055, 1020

REFERENCE EXAMPLE 3

3-Hexadecyloxy-2-hydroxypropyl 1,1-dimethylpiperidinio-3-yl phosphate

In 30 ml of ethanol was dissolved 243 mg of the benzylether prepared in Reference Example 2, and 20 mg of palladium(5%)-carbon (catalyst) was added to the resulting solution. The mixture was stirred overnight at 50° C. in a stream of hydrogen. The reaction liquid was cooled, and the catalyst was removed by filtration. The mothor liquer was concentrated under reduced pressure to give 163 mg of the desired compound.

$^1$H NMR (CD$_3$OD) δ: 0.90 (t, 3H), 1.29 (s, 26H), 1.3-4.7 (m, 24H)

IR (KBr) cm$^{-1}$: 3450, 2930, 2860, 1470, 1230, 1090, 1060

REFERENCE EXAMPLE 4

1,1-Dimethyl-4-hydroxypiperidinium p-toluenesulfonate

The procedures of Reference Example 1 were repeated using 1.16 g of 1-methyl-4-piperidinol and 1.18 g of methyl p-toluenesulfonate to give 2.62 g of the desired compound, m.p. 139°-140° C. (decomp.).

$^1$H NMR (DMSO-d$_6$) δ: 1.3-2.2 (m, 4H), 2.28 (s, 3H), 3.05 (s, 6H), 3.0-3.6 (m, 4H), 3.6-3.9 (m, 1H), 5.03 (d, 1H), 6.9-7.6 (m, 4H)

IR (KBr) cm$^{-1}$: 3360, 3015, 2900, 2875, 1475, 1205, 1190, 1120, 1100, 1030, 1005, 910, 810, 680, 560

REFERENCE EXAMPLE 5

2-Benzyloxy-3-hexadecyloxypropyl 1,1-dimethylpiperidinio-4-yl phosphate

The procedures of Reference Example 2 were repeated using 366 mg of 2-benzyloxy-3-hexadecyloxy-1-propanol, 407 mg of the quaternary salt prepared in Reference Example 4, 0.10 ml of phosphorus oxychloride, 0.31 ml of triethylamine, 7 ml of chloroform having been passed through an alumina column, and 8 ml of dry pyridine except that the reaction with the quaternary salt was carried out under application of ultrasonic wave, to give 109 mg of the desired compound.

$^1$H NMR (CD$_3$OD) δ: 0.89 (t, 3H), 1.28 (s, 26H), 1.3-4.5 (m, 24H), 4.69 (s, 2H), 7.1-7.4 (m, 5H)

IR (KBr) cm$^{-1}$: 3430, 3030, 2940, 2870, 1470, 1240, 1110, 1090, 1065, 1045, 1010, 930, 865

REFERENCE EXAMPLE 6

3-Hexadecyloxy-2-hydroxypropyl 1,1-dimethylpiperidinio-4-yl phosphate

The procedures of Reference Example 3 were repeated using 91 mg of the benzylether prepared in Reference Example 5, 18 mg of palladium(5%)-carbon and 9 ml of ethanol, to give 67 mg of the desired compound.

$^1$H NMR (CD$_3$OD) δ: 0.89 (t, 3H), 1.28 (s, 26H), 1.3-4.5 (m, 24H)

IR (KBr) cm$^{-1}$: 3430, 2920, 2850, 1470, 1220, 1100, 1080, 1060, 1040, 1010, 925

REFERENCE EXAMPLE 7

1,1-Dimethyl-3-hydroxypyrrolidinium p-toluenesulfonate

The procedures of Reference Example 1 were repeated using 1.01 g of 1-methyl-3-pyrrodinol and 1.86 g of methyl p-tolutenesolfonate, to give 2.17 g of the desired compound, 105°–107° C. (decomp.).

$^1$H NMR (DMSO-d$_6$) δ: 1.6–2.2 (m, 2H), 2.29 (s, 3H), 3.11 (s, 3H), 3.20 (s, 3H), 3.2–3.9 (m, 4H), 4.3–4.7 (m, 1H), 5.59 (d, 1H), 6.9–7.6 (m, 4H)

IR (KBr) cm$^{-1}$: 3400, 3050, 2950, 1450, 1180, 1120, 1035, 1010, 810, 680

REFERENCE EXAMPLE 8

2-Benzyloxy-3-hexadecyloxybutyl 1,1-dimethylpyrrolidinio-3-yl phosphate

The procedures of Reference Example 2 were repeated using 419 mg of 2-benzyloxy-3-hexadecyloxy-1-butanol, 480 mg of the quaternary salt prepared in Reference Example 7, 0.1 ml of phosphorus oxychloride, 0.3 ml of triethylamine, 7 ml of chloroform having been passed through an alumina column, and 8 ml of dry pyridine, to give 150 mg of the desired compound.

$^1$H NMR (CD$_3$OD) δ: 0.89 (t, 3H), 1.18 (d, 3H), 1.28 (s, 26H), 1.3–2.6 (m, 4H), 2.95–4.1 (m, 17H), 4.68 (s, 2H), 7.1–7.4 (m, 5H)

IR (neat) cm$^{-1}$: 3450, 3010, 2910, 2850, 1460, 1370, 1240, 1090, 1060, 1020, 940, 920, 880, 800, 750

REFERENCE EXAMPLE 9

3-Hexadecyloxy-2-hydroxybutyl 1,1-dimethylpyrrolidinio-3-yl phosphate

The procedures of Reference Example 3 were repeated using 150 mg of the benzylether prepared in Reference Example 8, 30 mg of palladium(5%)-carbon and 20 ml of ethanol, to give 130 mg of the desired compound.

$^1$H NMR (CD$_3$OD) δ: 0.89 (t, 3H), 1.05–1.2 (m, 3H), 1.28 (s, 26H), 1.3–2.6 (m, 4H), 3.1–4.0 (m, 17H)

IR (KBr) cm$^{-1}$: 3300, 2900, 2845, 1460, 1350, 1220, 1060, 1010, 940, 920, 885, 800, 720

REFERENCE EXAMPLE 10

2-Benzyloxy-3-hexadecyloxybutyl 1,1-dimethylpiperidinio-3-yl phosphate

The procedures of Reference Example 2 were repeated using 631 mg of 2-benzyloxy-3-hexadecyloxy-1-butanol, 678 mg of the quaternary salt prepared in Reference Example 1, 0.18 ml of phosphorus oxychloride, 0.52 ml of triethylamine, 9 ml of chloroform having been passed through an alumina column, and 15 ml of dry pyridine, to give 527 mg of the desired compound.

$^1$H NMR (CD$_3$OD) δ: 0.89 (t, 3H), 1.18 (d, 3H), 1.28 (s, 26H), 1.3–4.6 (m, 23H), 4.71 (s, 2H), 7.1–7.6 (m, 5H)

IR (KBr) cm$^{-1}$: 3400, 2920, 2840, 1480, 1460, 1450, 1225, 1080, 1060, 1020, 965

REFERENCE EXAMPLE 11

3-Hexadecyloxy-2-hydroxybutyl 1,1-dimethylpiperidinio-3-yl phosphate

The procedures of Reference Example 3 were repeated using 510 mg of the benzylether prepared in Reference Example 10, 50 mg of palladium(10%)-carbon and 15 ml of methanol, to give 396 mg of the desired compound.

$^1$H NMR (CD$_3$OD) δ: 0.90 (t, 3H), 1.18 (d, 3H), 1.29 (s, 26H), 1.3–4.8 (m, 23H)

IR (KBr) cm$^{-1}$: 3400, 2905, 2840, 1475, 1460, 1450, 1230, 1100, 1080, 1060, 1020, 970

REFERENCE EXAMPLE 12

2-Benzyloxy-3-hexadecyloxybutyl 1,1-dimethylpiperidino-4-yl phosphate

The procedures of Reference Example 2 were repeated using 2,100 mg of 2-benzyloxy-3-hexadecyloxy-1-butanol, 2480 mg of the quaternary salt prepared in Reference Example 4, 0.5 ml of phosphorus oxychloride, 1.5 ml of triethylamine, 30 ml of chloroform having been passed through an alumina column, and 40 ml of dry pyridine, to give 420 mg of the desired compound.

$^1$H NMR (CD$_3$OD) δ: 0.90 (t, 3H), 1.0–1.2 (m, 3H), 1.28 (s, 26H), 1.3–4.5 (m, 23H), 4.70 (s, 2H), 7.2–7.5 (m, 5H)

IR (KBr) cm$^{-1}$: 3400, 2920, 2850, 1460, 1380, 1230, 1070, 1040, 1000, 920, 855, 740, 700, 660

REFERENCE EXAMPLE 13

3-Hexadecyloxy-2-hydroxybutyl 1,1-dimethylpiperidinio-4-yl phosphate

The procedures of Reference Example 3 were repeated using 400 mg of the benzylether prepared in Reference Example 12, 140 mg of palladium(10%)-carbon and 30 ml of methanol, to give 260 mg of the desired compound.

$^1$H NMR (CD$_3$OD) δ: 0.89 (t, 3H), 1.0–1.3 (m, 3H), 1.28 (s, 26H), 1.3–4.5 (m, 23H)

IR (KBr) cm$^{-1}$: 3400, 2910, 2850, 1465, 1440, 1370, 1325, 1290, 1240, 1160, 1100, 1070, 1030, 1010, 980, 960, 920, 855, 835, 800, 720

REFERENCE EXAMPLE 14

(1) 2-Benzyloxy-1-hexadecyloxy-4-methyl-3-pentanol

To a solution of 3.05 g of oxalyl chloride in 40 ml of dry methylene chloride chilled with a dry ice- acetone bath was portionwise added under nitrogen atmosphere a solution of 3.75 g of dimethylsulfoxide in 10 ml of methylene chloride. The above addition was carried out keeping the oxalyl chloride solution at a temperature (inner temperature) below −60° C. To this solution was added a solution of 3.25 g of 2-benzyloxy-3-hexadecyloxy-1-propanol in 20 ml of methylene chloride, and then the dry ice-acetone bath was removed to allow the reaction solution to reach −10° C. The reaction solution was again chilled to −50° C. and, after addition of 5.28 g of triethylamine, allowed to reach 25° C. The reaction liquid was poured into 100 ml of water, and the separated organic layer was taken out. The organic layer was washed successively with 1N hydrochloric acid and aqueous saturated sodium hydrogencarbonate solution, and dried over anhydrous sodium sulfate. The solvent was removed under reduced pressure, and the residue was dissolved in 40 ml of dry tetrahydrofuran. Under nitrogen atmosphere, 8.0 ml of 2.0M isopropyl magnesium chloride-containing tetrahydrofuran was portionwise added to the above solution, keeping the inner temperature of the solution below 8° C. by chilling the solution with ice. The mixture was stirred overnight at room temperature. To the mixture (under chilling with ice) was portionwise added 16 ml of 1N hydrochloric acid, and further added ether. The organic layer was separated. The aqueous layer was then extracted with ether. The organic layer and the ether extract were combined, washed successively with an aqueous saturated sodium hydrogencarbonate solution and an aqueous saturated sodium chloride solution, and dried over anhydrous sodium sulfate. The solvent was distilled off, and the residue was purified by chromatography using silica gel (eluent: n-hexane/ethyl acetate=4/1) to give 2.16 g of the desired compound (mixture of isomers).

$^1$H NMR (CDCl$_3$) δ: 0.7-1.1 (m, 9H), 1.26 (s, 26H), 1.3-2.0 (m, 3H), 2.36 (m, 1H), 3.0-3.8 (m, 6H), 4.69 (m, 2H), 7.32 (s, 5H)

IR (neat) cm$^{-1}$: 3450, 2925, 2860, 1460, 1450, 1100, 1060, 690

(2) 2-Benzyloxy-3-(t-butyldimethyl)silyloxy-1-hexadecyloxy-4-methylpentane

In 17 ml of dry dimethylformamide were dissolved 1.31 g of the alcohol prepared in the (1) above, 497 mg of imidazole and 528 mg of t-butyldimethylchlorosilane under nitrogen atmosphere, and the mixture was heated under stirring to 60° C. for 40 hours. The solvent was distilled off under reduced pressure, and to the residue were added successively 50 ml of n-hexane and anhydrous sodium sulfate. The n-hexane solution was separated by decantation and concentrated under reduced pressure to give a residue. The residue was purified by chromatography using a silica gel (eluent: n-hexane/ethyl acetate=20/1), to give 1.31 g of the desired compound as a colorless oil.

$^1$H NMR (CDCl$_3$) δ: 0.00 (d, 6H, J=2.6 Hz), 0.8-1.0 (m, 18H, including =0.89 (s)), 1.26 (s, 26H), 1.3-2.0 (m, 3H), 3.40 (t, 2H, J=6.4 Hz), 3.4-3.7 (m, 4H), 4.67 (m, 2H), 7.31 (s, 5H)

IR (neat) cm$^{-1}$: 2930, 2860, 1460, 1250, 1115, 835, 770

(3) 3-(t-Butyldimethyl)silyloxy-1-hexadecyloxy-4-methyl-2-pentanol

In 25 ml of ethanol was dissolved 1,300 mg of the benzylether prepared in the (2) above, and to the solution was added 50 mg of palladium(5%)-carbon (catalyst). The mixture was stirred overnight at 50° C. in a stream of hydrogen. The catalyst was filtered off, and the mother liquer was concentrated under reduced pressure to give 1.09 g of the desired compound as a colorless oil.

$^1$H NMR (CDCl$_3$) δ: 0.10 (s, 6H), 0.7-1.0 (m, 18H, including δ=0.92 (s)), 1.26 (s, 26H), 1.3-1.9 (m, 3H), 2.4-2.6 (m, 1H), 3.2-3.8 (m, 6H)

IR (neat) cm$^{-1}$: 3550, 2920, 2850, 1455, 1245, 1110, 1060, 830, 765

(4) 2-Acetyloxy-3-(t-butyldimethyl)silyloxy-1-hexadecyloxy-4-methylpentane

In 20 ml of dry ethylene chloride were dissolved 236 mg of the alcohol prepared in the (3) above, 103 mg of pyridine and 10 mg of 4-dimethylaminopyridine under nitrogen atmosphere. To the mixture was added 92 mg of acetic anhydride, and the resulting mixture was heated under stirring to 60° C. for 23 hours. The solvent was removed under reduced pressure, and 30 ml of methylene chloride was added to the residue. The residue in methylene chloride was washed successively with an aqueous 15% potassium hydrogensulfate solution and an aqueous saturated sodium chloride solution, and dried over anhydrous sodium sulfate. The solvent was distilled off to give 257 mg of the desired compound as a colorless oil.

$^1$H NMR (CDCl$_3$) δ: 0.08 (d, 6 H, J=1 Hz), 0.7-1.0 (m, 18H, including δ=0.90 (s)), 1.26 (s, 26H), 1.3-1.8 (m, 3H), 2.07 (s, 3H), 3.1-3.7 (m, 5H), 4.8-5.05 (m, 1H)

IR (neat) cm$^{-1}$: 2950, 2870, 1745, 1460, 1370, 1240, 1120, 1065, 840, 775

(5) 3-Acetyloxy-1-hexadecyloxy-4-methyl-3-pentanol

In 3 ml of dry chloroform was dissolved 257 mg of the silylether prepared in the (4) above, and 0.25 g of boron trifluoride-ethyl ether complex was added to the resulting solution. The mixture was stirred overnight at room temperature. The reaction solution was mixed with an aqueous 5% sodium hydrogencarbonate solution, and stirred. The separated organic layer was collected, and dried over anhydrous sodium sulfate. The solvent was distilled off to give 200 mg of the desired compound as a colorless oil.

$^1$H NMR (CDCl$_3$) δ: 0.7-1.1 (m, 9H), 1.26 (s, 26H), 1.3-1.8 (m, 3H), 2.10 (s, 3H), 2.2-2.7 (br, 1H), 3.1-3.6 (m, 4H), 3.6-4.0 (m, 1H), 4.6-5.1 (m, 1H)

IR (neat) cm$^{-1}$: 3460, 2920, 2850, 1745, 1460, 1370, 1240, 1115, 1030

REFERENCE EXAMPLE 15

3-Benzyloxy-4-hexadecyloxy-2-pentanol

To a solution of 1.37 g of oxalyl chloride in 29 ml of dry methylene chloride chilled with a dry ice-acetone bath was portionwise added under nitrogen atmosphere a solution of 1.69 g of dimethylsulfoxide in 7 ml of methylene chloride. The above addition was carried out keeping the oxalyl chloride solution at a temperature (inner temperature) below −60° C. To this solution was added a solution of 1,514 mg of 2-beyzyloxy-3-hexadecyloxy-1-butanol in 15 ml of methylene chloride, and then the dry ice-acetone bath was removed to allow the reaction solution to reach −10° C. The reaction solution was again chilled to −50° C. and, after addition of 2,368 mg of triethylamine, allowed to reach 25° C. The reaction liquid was poured into 35 ml of water, and the separated organic layer was taken out. The organic layer was washed with 1N hydrochloric acid, and dried over anhydrous sodium sulfate. The solvent was removed under reduced pressure, and the residue was dissolved in 29 ml of dry tetrahydrofuran. Under nitrogen atmosphere, 3.6 ml of 2.0M methyl magnesium iodide- containing tetrahydrofuran was portionwise added to the above solution, under chilling the solution with ice. The mixture was stirred overnight at room temperature. To the mixture (under chilling with ice) was portionwise added 10 ml of 1N hydrochloric acid, and further added ether. The organic layer was separated. The aqueous layer was then extracted with ether. The organic layer and the ether extract were combined, washed successively with an aqueous saturated sodium hydrogencarbonate solution and an aqueous saturated sodium chloride solution, and dried over anhydrous sodium sulfate. The solvent was distilled off, and the residue was purified by chromatography using silica gel (eluent: n-hexane/ethyl acetate=25/2) to give 1,225 mg of the desired compound (mixture of isomers).

MS (m/e): 434 (M$^+$)

$^1$H NMR (CDCl$_3$) δ: 0.6–1.7 (m, 37H), 2.3–3.1 (m, 1H), 3.0–4.1 (m, 5H), 4.4–4.8 (m, 2H), 7.32 (s, 5H)

REFERENCE EXAMPLE 16

2-Benzyloxy-3-hexadecyloxy-1-methylbutyl 1,1-dimethylpyrrolidinio-3-yl phosphate The procedures of Reference Example 2 were repeated using 528 mg of the hydroxyl product prepared in Reference Example 15, 523 mg of the quaternary salt prepared in Reference Example 7, 0.14 ml of phosphorus oxychloride, 0.42 ml of triethylamine, 7 ml of chloroform having been passed through an alumina column, and 11 ml of dry pyridine, to give 431 mg of the desired compound (mixture of isomers).

$^1$H NMR (CD$_3$OD) δ: 0.9 (t, 3H), 1.0–1.7 (m, 34H), 2.2–2.7 (m, 2H), 2.9–4.0 (m, 14H), 4.2–5.1 (m, 4H), 7.1–7.5 (m, 5H)

REFERENCE EXAMPLE 17

3-Hexadecyloxy-2-hydroxy-1-methylbutyl 1,1-dimethylpyrrolidinio-3-yl phosphate

The procedures of Reference Example 3 were repeated using 233 mg of the benzylether prepared in Reference Example 16, 20 mg of palladium(5%)-carbon and 10 ml of ethanol, to give 141 mg of the desired compound.

$^1$H NMR (CD$_3$OD/CDCl$_3$=3/2) δ: 0.89 (t, 3H), 1.0–1.7 (m, 34H), 2.3–2.7 (m, 2H), 3.1–5.1 (m, 16H)

IR (KBr) cm$^{-1}$: 3400, 2925, 2850, 1470, 1215, 1070

REFERENCE EXAMPLE 18

2-Benzyloxy-3-hexadecyloxypropyl 1,1-dimethylpyrrolidinio-3-yl phosphate

In 3 ml of chloroform having been passed through alumina were dissolved 0.1 ml of phosphorus oxychloride and 0.31 ml of triethylamine under nitrogen atmosphere, and the resulting solution was stirred for a while at room temperature. To the solution was dropwise added under chilling 2 ml of a solution of 366 mg of 2-benzyloxy-3-hexadecyloxy-1-propanol in chloroform (treated as above). After the addition was complete, the mixture was stirred for 30 minutes at room temperature, and to the mixture were added 388 mg of the quaternary salt prepared in Reference Example 7 and 8 ml of dry pyridine. The mixture was stirred overnight at room temperature, and to the mixture were added 500 mg of sodium hydrogencarbonate and 1.25 ml of water. The solvent was then distilled off under reduced pressure. To the residue were added 5 ml of toluene and 5 ml of methylene chloride, and the insolubles were filtered off. The mother liquor was concentrated under reduced pressure, and the resulting residue was dissolved in a mixture of tetrahydrofuran and water (v/v=95/5). The solution was passed through a column of ion-exchange resin (Amberlite MB-3), which was then eluated with the same mixture of tetrahydrofuran and water. The eluate was placed under reduced pressure to distill off the solvent. The residue was purified by column chromatography using silica gel (eluent: chloroform/methanol/water=70/30/5) to obtain 298 mg of the desired compound as a colorless solid. Yield 56.8%.

$^1$H NMR (CD$_3$OD) δ: 0.89 (t, 3H), 1.28 (s, 26H), 1.3–1.7 (m, 2H), 2.2–2.6 (m, 2H), 2.8–4.1 (m, 17H), 4.69 (s, 2H), 4.8–5.1 (m, 1H), 7.1–7.5 (m, 5H)

IR (KBr) cm$^{-1}$: 3400, 3060, 3030, 2920, 2850, 1450, 1230, 1110, 1070

REFERENCE EXAMPLE 19

3-Hexadecyloxy-2-hydroxypropyl 1,1-dimethylpyrrolidinio-3-yl phosphate

In 15 ml of ethanol was dissolved 175 mg of the benzylether prepared in Reference Example 18, and 15 mg of palladium(5%)-carbon (catalyst) was added to the resulting solution. The mixture was stirred overnight at 50° C. in a stream of hydrogen. The reaction liquid was cooled, and the catalyst was removed by filtration. The mothor liquor was concentrated under reduced pressure to give 146 mg of the desired compound as a white solid. Yield 98.6%.

$^1$H NMR (CD$_3$OD/CDCl$_3$=1/3) δ: 0.88 (t, 3H), 1.26 (s, 26H), 1.3–1.7 (m, 2H), 2.3–2.7 (m, 2H), 2.9–4.1 (m, 17H), 4.8–5.1 (m, 1H)

IR (KBr) cm$^{-1}$: 3400, 2920, 2850, 1460, 1230, 1095, 1060

EXAMPLE 1

2-Acetyloxy-3-hexadecyloxypropyl 1,1-dimethylpiperidinio-3-yl phosphate

In 10 ml of chloroform were dissolved 134 mg of the hydroxyl compound prepared in Reference Example 3 and 674 mg of acetic anhydride. To the solution was added 267 mg of triethylamine, and the resulting mixture was heated overnight under reflux. The solvent was distilled off under reduced pressure, and the resulting residue was purified using silica gel column chromatography (eluent: chloroform/methanol/water=70/30/5) to give 130 mg of the desired compound.

$^1$H NMR (CD$_3$OD) δ: 0.90 (t, 3H), 1.28 (s, 26H), 1.3–2.2 (m, 3H), 2.06 (m, 3H), 2.8–4.7 (m, 17H), 5.0–5.3 (m, 1H)

IR (KBr) cm$^{-1}$: 3450, 2930, 2855, 1740, 1470, 1380, 1240, 1090, 1070, 1025, 975

EXAMPLE 2

2-Acetyloxy-3-hexadecyloxypropyl 1,1-dimethylpiperidinio-4-yl phosphate

The procedures of Example 1 were repeated using 48 mg of the hydroxyl compound prepared in Reference Example 6, 242 mg of acetic anhydride, 96 mg of triethylamine and 5 ml of chloroform to give 24 mg of the desired compound.

$^1$H NMR (CD$_3$OD/CDCl$_3$=10/1) δ: 0.89 (t, 3H), 1.28 (s, 26H), 1.3–2.3 (m, 6H), 2.06 (m, 3H), 2.8–4.5 (m, 17H), 4.9–5.2 (m, 1H)

IR (KBr) cm$^{-1}$: 3420, 2920, 2850, 1730, 1460, 1375, 1240, 1100, 1080, 1035, 1005, 920

EXAMPLE 3

2-Acetyloxy-3-hexadecyloxybutyl 1,1-dimethylpyrrolidinio-3-yl phosphate

The procedures of Example 1 were repeated using 100 mg of the hydroxyl compound prepared in Reference Example 9, 2 ml of acetic anhydride, 0.5 mg of dry pyridine and 5 ml of ethylene chloride to give 33 mg of the desired compound.

$^1$H NMR (CD$_3$OD) δ: 0.90 (t, 3H), 1.0–1.2 (m, 3H), 1.28 (s, 26H), 1.3–2.7 (m, 4H), 2.04 (s, 3H), 3.1–4.3 (m, 16H), 4.9–5.1 (m, 1H)

IR (KBr) cm$^{-1}$: 3400, 2920, 2850, 1730, 1460, 1370, 1240, 1070, 1020, 940, 920, 890, 800

EXAMPLE 4

2-Acetyloxy-3-hexadecyloxybutyl
1,1-dimethylpiperidinio-3-yl phosphate

The procedures of Example 1 were repeated using 876 mg of the hydroxyl compound prepared in Reference Example 11, 4186 mg of acetic anhydride, 1660 mg of triethylamine and 80 ml of chloroform to give 804 mg of the desired compound.

$^1$H NMR (CD$_3$OD) δ: 0.9 (t, 3H), 1.15 (d, 3H), 1.28 (s, 26H), 1.3–2.05 (m, 6H), 2.07 (s, 3H), 3.1–4.7 (m, 16H), 4.8–5.2 (m, 1H)

IR (KBr) cm$^{-1}$: 3400, 2920, 2850, 1730, 1465, 1375, 1240, 1120, 1105, 1090, 1075, 1050, 1020, 970

EXAMPLE 5

2-Acetyloxy-3-hexadecyloxybutyl
1,1-dimethylpiperidinio-4-yl phosphate

The procedures of Example 1 were repeated using 250 mg of the hydroxyl compound prepared in Reference Example 13, 1220 mg of acetic anhydride, 450 mg of triethylamine and 25 ml of chloroform to give 160 mg of the desired compound.

$^1$H NMR (CD$_3$OD)δ: 0.9 (t, 3H), 1.0–1.3 (m, 3H), 1.28 (s, 26H), 1.3–2.3 (m, 6H), 2.06 (s, 3H), 3.0–4.6 (m, 16H), 4.9–5.1 (m, 1H)

IR (KBr) cm$^{-1}$: 3400, 2910, 2850, 1730, 1460, 1370, 1320, 1240, 1160, 1070, 1035, 1000, 950, 920, 850, 830, 660

EXAMPLE 6

2-Acetyloxy-3-hexadecyloxy-1-(1-methylethyl)-propyl
1,1-dimethylpyrrolidinio-3-yl phosphate The procedures of Reference Example 2 were repeated using 485 mg of the hydroxyl compound prepared in Reference Example 14-(5), 523 mg of the quaternary salt prepared in Reference Example 7, 0.14 ml of phosphorus oxychloride, 0.42 ml of triethylamine, 7 ml of chloroform having been passed through an alumina column, and 11 ml of dry pyridine to give 147 mg of the desired compound.

$^1$H NMR (CD$_3$OD/CDCl$_3$=⅓) δ: 0.7–1.1 (m, 9H), 1.27 (s, 26H), 1.3–1.7 (m, 3H), 2.10 (s, 3H), 2.3–4.1 (m, 16H), 4.2–4.6 (m, 1H), 4.8–5.1 (m, 2H)

IR (KBr) cm$^{-1}$: 3420, 2925, 2855, 1735, 1470, 1370, 1240, 1100, 1075, 1030

EXAMPLE 7

2-Acetyloxy-3-hexadecyloxy-1-methylbutyl
1,1-dimethylpyrrolidinio-3-yl phosphate The procedures of Example 1 were repeated using 58 mg of the hydroxyl compound prepared in Reference Example 17, 281 mg of acetic anhydride, 111 mg of triethylamine, 10 mg of 4-dimethylaminopyridine and 10 ml of chloroform to give 160 mg of the desired compound.

$^1$H NMR (CD$_3$OD) δ: 0.90 (t, 3H), 1.0–1.2 (m, 6H), 1.29 (s, 26H), 1.3–2.7 (m, 4H), 2.03, 2.09 (sx2, 3H), 2.9–4.0 (m, 12H), 4.7–5.2 (m, 4H).

IR (KBr) cm$^{-1}$: 3400, 2925, 2855, 1735, 1470, 1375, 1240, 1070, 1020

EXAMPLE 8

2-Acetyloxy-3-hexadecyloxypropyl
1,1-dimethylpyrrolidinio-3-yl phosphate

In 5 ml of ehtylene chloride were dissolved 99 mg of the hydroxyl compound prepared in Reference Example 19 and 2 ml of acetic anhudride. The resulting solution was chilled with ice, and 0.5 ml of pyridine was added. The resulting mixture was stirred overnight at 70° C. The solvent was distilled off under reduced pressure, and the resulting residue was purified using a silica gel column chromatography (eluent: chloroform/methanol/water =70/30/5) to give 83 mg of the desired compound as a wax. Yield 77.6%.

$^1$H NMR (CD$_3$OD) δ: 0.90 (t, 3H), 1.28 (s, 26H), 1.3–1.7 (m, 2H), 2.06 (s, 3H), 2.3–7.3 (m, 2H), 2.9–4.1 (m, 18H)

IR (KBr) cm$^{-1}$: 3400, 2910, 2840, 1730, 1450, 1230, 1060

EXAMPLE 9

Pellets

| | | |
|---|---|---|
| (1) 2-Acetyloxy-3-hexadecyloxybutyl 1,1-dimethylpyrrolidinio-3-yl phosphate | | 1.0 g |
| (2) Lactose | | 27.0 g |
| (3) Crystalline cellulose | | 20.0 g |
| (4) Corn starch | | 5.0 g |
| (5) Carboxymethylcellulose calcium | | 5.0 g |
| (6) Hydroxypropylcellulose | | 1.6 g |
| (7) Magnesium stearate | | 0.4 g |

A mixture of the components (1) to (6) was processed in the conventional manner to prepare granules, and the granules were then mixed with the component (7). The mixture was processed to form pellets (60 mg for one pellet which contained 1 mg of the component (1)).

EXAMPLE 10

Injections

In 10 liters of a distilled water for injection were dissolved 1.0 mg of 2-acetyloxy-3-hexadecyloxypropyl 1,1-dimethylpiperidinio-3-yl phosphate and 100 g of mannitol. The solution was filtered under sterile condition, and the filtrate was divided into a plurality of 5 ml vials in an amount of 0.5 ml for one vial. The divided portions were freeze-dried in the conventional manner and then the vials were sealed tightly to give a freeze-dried agent for injection.

EXAMPLE 11

Soft Capsules

| | |
|---|---|
| (1) 2-Acetyloxy-3-hexadecyloxybutyl 1,1-dimethylpyrrolidinio-3-yl phosphate | 0.1 g |
| (2) Polyethylene glycol 400 | 169.9 g |
| (3) Polyvinyl pyrrolidone | 5.0 g |
| (4) Glycerol | 75.0 g |

The components (1) to (4) was mixed to give a homogeneous solution. The solution was enclosed with gelatin sheets to give soft capsules containing 100 μg of the component (1) in one capsule.

We claim:

1. A glycerol derivative having the formula:

$$\begin{array}{c} R^5-CH-OR^1 \\ | \\ R^6-C-OR^2 \quad O \\ | \quad \quad \quad || \\ R^7-CH-O-P-O-CH \\ | \\ O^{\ominus} \end{array} \begin{array}{c} (CH_2)_m \\ \diagdown \\ \oplus N \\ \diagup \\ (CH_2)_n \end{array} \begin{array}{c} R^3 \\ \\ R^4 \end{array}$$

wherein $R^1$ is a straight or branched chain alkyl group having 10-22 carbon atoms;

$R^2$ is a straight or branched chain acyl group having 1-6 carbon atoms or benzoyl;

each of $R^3$ and $R^4$ independently is hydrogen or a straight or branched chain alkyl group having 1-6 carbon atoms;

each of $R^5$, $R^6$ and $R^7$ independently is hydrogen, a straight or branched chain alkyl group having 1-6 carbon atoms, a phenyl, toluyl, or xylyl group or a benzyl or phenylethyl group; and each of m and n independently is zero or a positive integer under the condition of n+m=3-5.

2. The glycerol derivative as claimed in claim 1, wherein $R^1$ is a straight or branched chain alkyl having 12-20 carbon atoms.

3. The glycerol derivative as claimed in claim 1, wherein $R^2$ is a straight chain acyl having 2-6 carbon atoms.

4. The glycerol derivative as claimed in claim 1, wherein each of $R^3$ and $R^4$ independently is an alkyl group selected from the group consisting of methyl, ethyl, n-propyl and isopropyl.

5. The glycerol derivative as claimed in claim 1, wherein each of $R^5$, $R^6$ and $R^7$ is hydrogen.

6. The glycerol derivative as claimed in claim 1, wherein $R^5$ is a straight or branched chain alkyl having 1-6 carbon atoms, and each of $R^6$ and $R^7$ is hydrogen.

7. The glycerol derivative as claimed in claim 1, wherein $R^7$ is a straight or branched chain alkyl having 1-6 carbon atoms, and each of $R^5$ and $R^6$ is hydrogen.

8. A glycerol derivative having the formula:

$$\begin{array}{c} R^5-CH-OR^1 \\ | \\ R^6-C-OR^2 \quad O \\ | \quad \quad \quad || \\ R^7-CH-O-P-O-CH \\ | \\ O^{\ominus} \end{array} \begin{array}{c} (CH_2)_m \\ \diagdown \\ \oplus N \\ \diagup \\ (CH_2)_n \end{array} \begin{array}{c} R^3 \\ \\ R^4 \end{array}$$

wherein $R^1$ is a straight or branched chain alkyl group having 10-22 carbon atoms; each of $R^3$ and $R^4$ independently is hydrogen or a straight or branched chain alkyl group having 1-6 carbon atoms; each of $R^5$, $R^6$ and $R^7$ independently is hydrogen, a straight or branched chain alkyl group having 1-6 carbon atoms, a phenyl, toluyl, or xylyl group or a benzyl or phenylethyl group; and each of m and n independently is zero or a positive integer under the condition of n+m=3-5.

9. The glycerol derivative as claimed in claim 8, wherein $R^1$ is a straight or branched chain alkyl having 12-20 carbon atoms.

10. The glycerol derivative as claimed in claim 8, wherein each of $R^3$ and $R^4$ independently is an alkyl group selected from the group consisting of methyl, ethyl, n-propyl and isopropyl.

11. The glycerol derivative as claimed in claim 8, wherein each of $R^5$, $R^6$ and $R^7$ is hydrogen.

12. The glycerol derivative as claimed in claim 8, wherein each of $R^5$ is a straight or branched chain alkyl having 1-6 carbon atoms, and each of $R^6$ and $R^7$ is hydrogen.

13. A method for reducing blood pressure comprising administering to human in need of such treatment beings a glycerol derivative at a dose of 10 μg/kg to 0.5 mg/kg and having the formula:

$$\begin{array}{c} R^5-CH-OR^1 \\ | \\ R^6-C-OR^2 \quad O \\ | \quad \quad \quad || \\ R^7-CH-O-P-O-CH \\ | \\ O^{\ominus} \end{array} \begin{array}{c} (CH_2)_m \\ \diagdown \\ \oplus N \\ \diagup \\ (CH_2)_n \end{array} \begin{array}{c} R^3 \\ \\ R^4 \end{array}$$

wherein $R^1$ is a straight or branched chain alkyl group having 10-22 carbon atoms; $R^2$ is a straight or branched chain acyl group having 1-6 carbon atoms or benzoyl; each of $R^3$ and $R^4$ independently is hydrogen or a straight or branched chain alkyl group having 1-6 carbon atoms; each of $R^5$, $R^6$ and $R^7$ independently is hydrogen, a straight or branched chain alkyl group having 1-6 carbon atoms, a phenyl, toluyl, or xylyl group or a benzyl or phenylethyl group; and each of m and n independently is zero or a positive integer under the condition of n+m=3-5.

14. The method for reduction of blood pressure as claimed in claim 9, wherein $R^1$ is a straight or branched chain alkyl having 12-20 carbon atoms.

15. The method for reduction of blood pressure as claimed in claim 9, wherein $R^2$ is a straight chain acyl having 2-6 carbon atoms.

16. The method for reduction of blood pressure as claimed in claim 9, wherein each of $R^3$ and $R^4$ independently is an alkyl group selected from the group consisting of methyl, ethyl, n-propyl and isopropyl.

17. The method for reduction of blood pressure as claimed in claim 9, wherein each of $R^5$, $R^6$ and $R^7$ is hydrogen.

18. The method for reduction of blood pressure as claimed in claim 9, wherein $R^5$ is a straight or branched chain alkyl having 1-6 carbon atoms, and each of $R^6$ and $R^7$ is hydrogen.

19. The method for reduction of blood pressure as claimed in claim 9, wherein $R^7$ is a straight or branched chain alkyl having 1-6 carbon atoms, and each of $R^5$ and $R^6$ is hydrogen.

* * * * *